(12) United States Patent
Haskell et al.

(10) Patent No.: US 7,788,040 B2
(45) Date of Patent: Aug. 31, 2010

(54) SYSTEM FOR MANAGING HEALTHCARE DATA INCLUDING GENOMIC AND OTHER PATIENT SPECIFIC INFORMATION

(75) Inventors: Robert Emmons Haskell, Chester Springs, PA (US); Ernst Bartsch, Nürnberg (DE); Dorin Comaniciu, Princeton Jct., NJ (US); Mohammad Naraghi, Fürth (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 223 days.

(21) Appl. No.: 11/016,038

(22) Filed: Dec. 17, 2004

(65) Prior Publication Data

US 2005/0158767 A1 Jul. 21, 2005

Related U.S. Application Data

(60) Provisional application No. 60/531,208, filed on Dec. 19, 2003.

(51) Int. Cl.
*G01N 33/48* (2006.01)
*C12Q 1/68* (2006.01)
(52) U.S. Cl. ................. 702/19; 702/20; 435/6
(58) Field of Classification Search ............... None
See application file for complete search history.

(56) References Cited

U.S. PATENT DOCUMENTS

| 6,108,635 | A | 8/2000 | Herren et al. |
|---|---|---|---|
| 6,213,391 | B1 | 4/2001 | Lewis |
| 6,415,295 | B1 | 7/2002 | Feinberg |
| 6,551,243 | B2 | 4/2003 | Bocionek et al. |
| 6,742,004 | B2 | 5/2004 | Sabatini et al. |
| 6,804,679 | B2 | 10/2004 | Jevons et al. |
| 6,816,867 | B2 | 11/2004 | Jevons et al. |
| 7,158,892 | B2 * | 1/2007 | Robson et al. ............... 702/20 |
| 2003/0036110 | A1 | 2/2003 | Maertens et al. |
| 2003/0046114 | A1 | 3/2003 | Davies et al. |
| 2003/0233251 | A1 | 12/2003 | Haskell et al. |
| 2003/0233252 | A1 | 12/2003 | Haskell et al. |
| 2004/0133083 | A1 | 7/2004 | Comaniciu et al. |
| 2004/0193036 | A1 | 9/2004 | Zhou et al. |
| 2004/0215651 | A1 | 10/2004 | Markowitz et al. |

FOREIGN PATENT DOCUMENTS

EP 1 244 047 A2 9/2002

OTHER PUBLICATIONS

International Search Report (May 10, 2005).

* cited by examiner

*Primary Examiner*—Shubo (Joe) Zhou

(57) ABSTRACT

A system, for processing patient medical information for storage in an electronic patient medical record repository, includes an interface, a repository, and a data processor. The interface receives data representing genomic information of a patient. The repository includes a patient record incorporating data representing genomic information specific to a particular patient. A data processor compares the genomic information specific to a particular patient with the received genomic information. The data processor identifies a genomic match in response to the comparison and predetermined matching criteria. The data processor initiates processing of patient record information specific to the particular patient in response to an identified match.

12 Claims, 11 Drawing Sheets

1100

```
                    ┌─────────┐
                    │  START  │───1101
                    └─────────┘
                         │
                         ▼
┌──────────────────────────────────────────────────────┐
│ EXPLORE GENERAL CONTENT OF DISEASE-SPECIFIC DATA     │
│ MART WITH SIMPLE REPORTING TOOLS TO UNDERSTAND       │───1102
│ GENERAL CONTENT OF THE DATA MART (E.G., PATIENT      │
│ LISTINGS).                                           │
└──────────────────────────────────────────────────────┘
                         │
                         ▼
┌──────────────────────────────────────────────────────┐
│ USE OLAP TOOL TO HELP UNDERSTAND SOME OF THE BASIC   │
│ PERFORMANCE CHARACTERISTICS OF THE PATIENTS AND      │───1103
│ RELATIONSHIPS BETWEEN DEPENDENT AND INDEPENDENT      │
│ VARIABLES.                                           │
└──────────────────────────────────────────────────────┘
                         │
                         ▼
┌──────────────────────────────────────────────────────┐
│ ONCE SOME BASIC CHARACTERISTICS AND ASSUMPTIONS      │
│ ABOUT THE DATA ARE UNDERSTOOD, USE MINING TOOLS IN   │───1104
│ THE CONTEXT OF THESE CONSTRAINTS                     │
└──────────────────────────────────────────────────────┘
                         │
                         ▼
┌──────────────────────────────────────────────────────┐
│ SEARCH FOR NEW RELATIONSHIPS TO HELP OPTIMIZE HEALTH │───1105
│ CARE DELIVERY AND TO PREDICT PATIENT BEHAVIOR AND    │
│ OUTCOMES.                                            │
└──────────────────────────────────────────────────────┘
                         │
                         ▼
┌──────────────────────────────────────────────────────┐
│ SET UP PERFORMANCE METRICS TO BE MONITORED ON A      │───1106
│ ROUTINE BASIS, INCLUDING THRESHOLDS OF APPROPRIATE   │
│ VARIATION.                                           │
└──────────────────────────────────────────────────────┘
                         │
                         ▼
┌──────────────────────────────────────────────────────┐
│ COMBINE DERIVED INTERNAL INFORMATION AND ESTABLISHED │
│ EXTERNAL KNOWLEDGE INTO MODELS AND RULES THAT HELP   │───1107
│ PREDICT AND DIRECT FUTURE BEHAVIOR.                  │
└──────────────────────────────────────────────────────┘
                         │
                         ▼
┌──────────────────────────────────────────────────────┐
│ APPLY THE MODELS AND RULES TO THE PROCESSES OF       │
│ HEALTH CARE DELIVERY AND CLINICAL RESEARCH, TO HELP  │───1108
│ OPTIMIZE THEIR EFFICIENCY AND QUALITY.               │
└──────────────────────────────────────────────────────┘
                         │
                         ▼
                    ┌─────────┐
                    │   END   │───1109
                    └─────────┘
```

FIG. 11

SYSTEM FOR MANAGING HEALTHCARE DATA INCLUDING GENOMIC AND OTHER PATIENT SPECIFIC INFORMATION

CROSS-REFERENCE TO RELATED APPLICATIONS

The present application is a non-provisional application of provisional application having Ser. No. 60/531,208 filed by Robert Haskell on Dec. 19, 2003.

FIELD OF THE INVENTION

The present invention generally relates to computer information systems. More particularly, the present invention relates to a system for managing healthcare data including genomic and other patient specific information.

BACKGROUND OF THE INVENTION

Present healthcare delivery operations are fragmented and diverse. Clinical decisions are made without the benefit of evidence-based best practice or reference cases, health care is provided without regard to the genetic characteristics of individual patients, and historical clinical data is fragmented, diverse, and generally not structured or organized to facilitate information retrieval and knowledge discovery. Existing healthcare systems typically operate within a single site or enterprise offering limited administrative, clinical, and financial data in both operational and informational contexts and are generally passive in nature. Further, existing healthcare systems react to data entered, but generally do not provide proactive guidance to the health professional end users of the systems. Accordingly, there is a need for a system for managing healthcare data including genomic and other patient specific information that overcomes these and other disadvantages of the prior systems.

SUMMARY OF THE INVENTION

A system, for processing patient medical information for storage in an electronic patient medical record repository, includes an interface, a repository, and a data processor. The interface receives data representing genomic information of a patient. The repository includes a patient record incorporating data representing genomic information specific to a particular patient. A data processor compares the genomic information specific to a particular patient with the received genomic information. The data processor identifies a genomic match in response to the comparison and predetermined matching criteria. The data processor initiates processing of patient record information specific to the particular patient in response to an identified match.

BRIEF DESCRIPTION OF THE DRAWINGS

FIG. 11 illustrates a mining and modeling method for the healthcare system, as shown in FIG. 2, in accordance with invention principles.

DETAILED DESCRIPTION OF THE PREFERRED EMBODIMENTS

Figure 1:
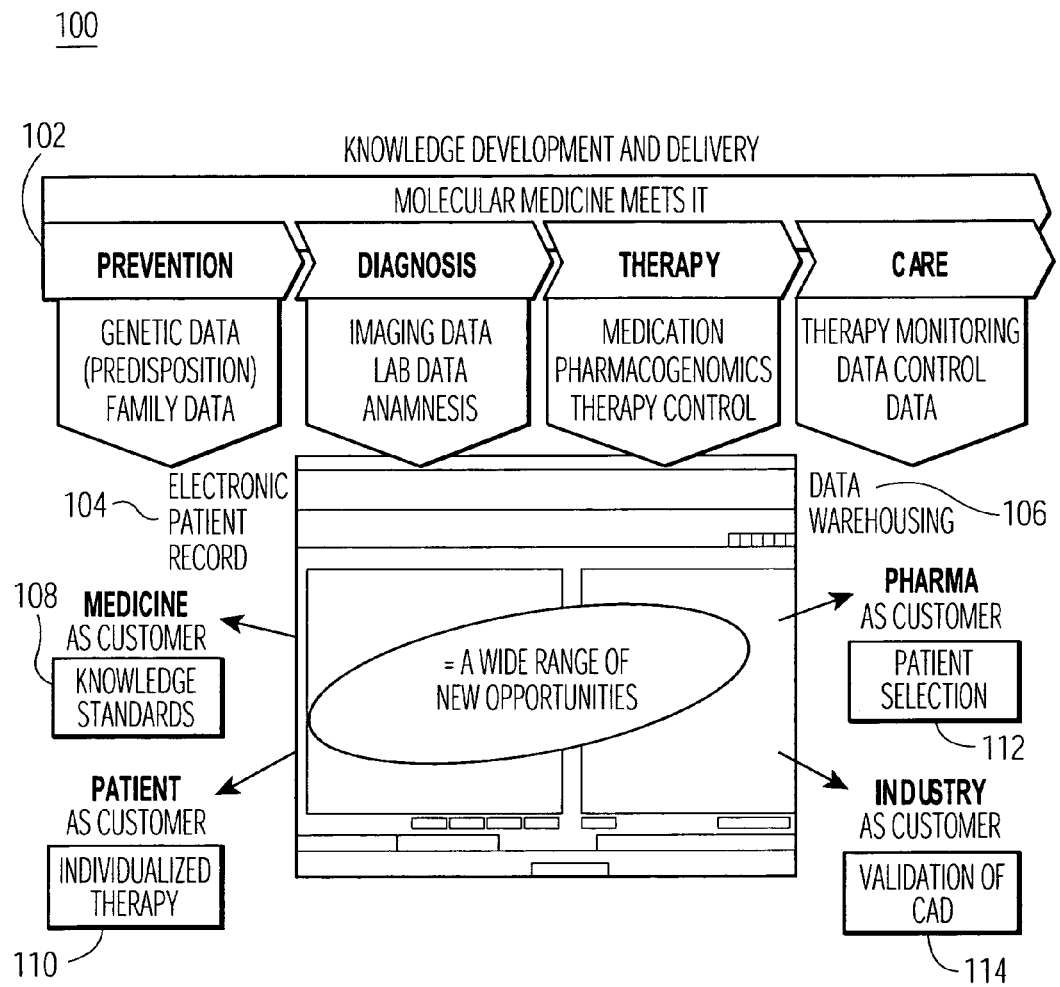
FIG. 1 illustrates a healthcare business model, in accordance with invention principles.

FIG. 1 illustrates a healthcare business model 100 that supports medical knowledge development and delivery using information technology ("IT"). The healthcare business model 100 provides services and solutions to help the healthcare industry improve the quality and efficiency of healthcare delivery to patients and to facilitate clinical research (e.g., for drug discovery and drug use). The healthcare information and knowledge to provide the services and solutions are derived or sourced from a healthcare delivery model 102, which includes prevention, diagnosis, therapy, and care for patients. The healthcare information and knowledge sourced from a healthcare delivery model 102 is stored in a resource, represented by an electronic patient record 104 and/or a data warehouse 106.

Use of the stored healthcare information and knowledge provides a wide range of new opportunities to improve the quality and efficiency of healthcare delivery to patients and to facilitate clinical research. Such opportunities concern, for example and without limitation, medicine 108, patient 110, pharmacology 112, and industry 114. For example, the services and solutions provided from the stored healthcare information and knowledge help to:

1. Implement preventive therapy or lifestyle changes based on "genetic predisposition" for disease.
2. Detect and control disease outbreak.
3. Establish efficient therapies with measurable outcomes.
4. Streamline and rationalize healthcare processes to reduce healthcare delivery costs.
5. Accelerate the pace of research.

Figure 2:
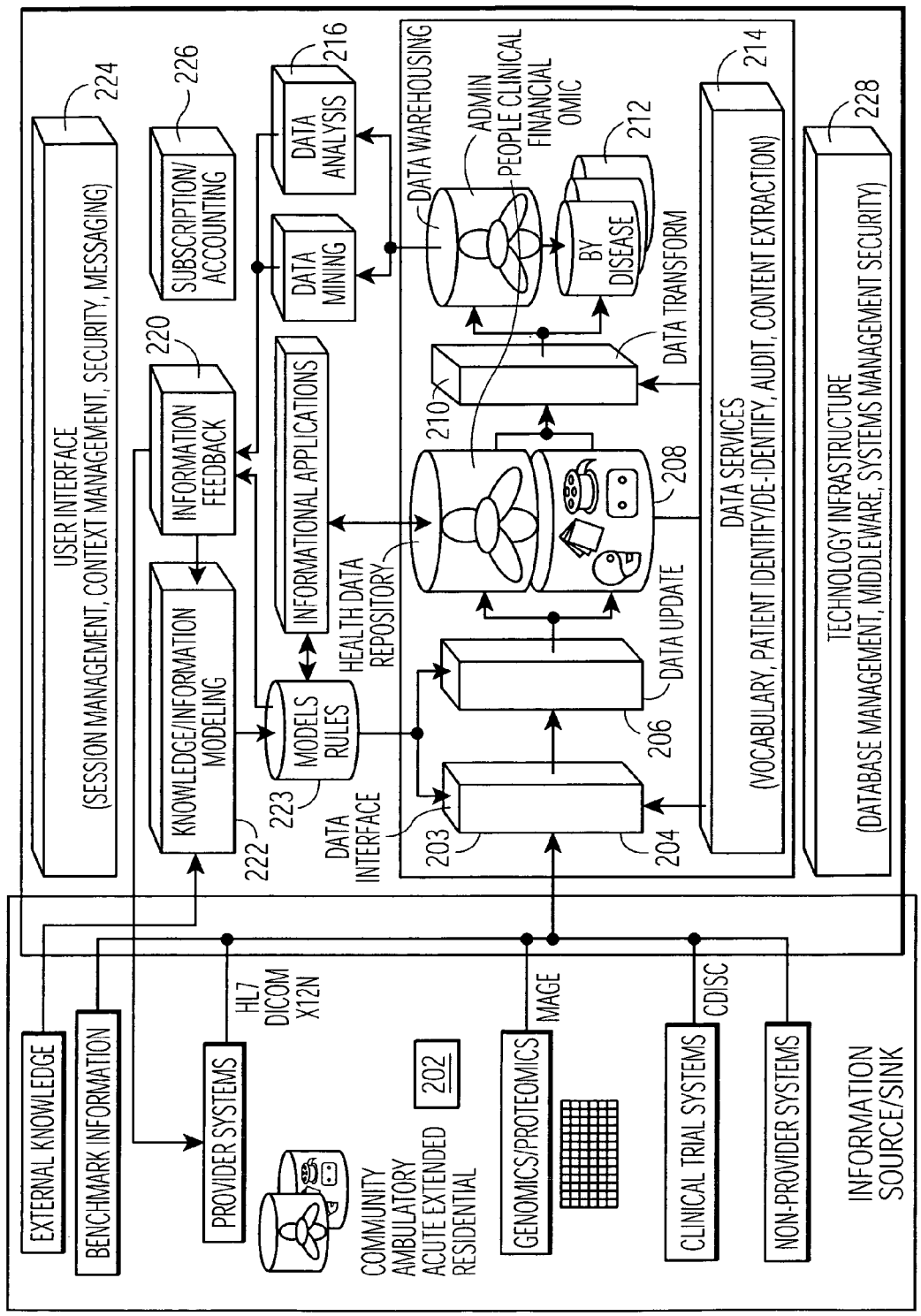
FIG. 2 illustrates a healthcare system for the healthcare business model, as shown in FIG. 1, in accordance with invention principles.

FIG. 2 illustrates a healthcare system 200 ("system") adapted to implement the healthcare business model 100, as shown in FIG. 1. The system 200 includes an information source/sink 202, a data interface processor 204, a data update processor 206, a health data repository 208, a data transform processor 210, a data warehouse 212, a data service processor 214, data mining and analysis processors 216, applications 218, feedback processor 220, a modeling processor 222, a user interface 224, a subscription/accounting processor 226, and technology infrastructure 228.

The system 200 may be employed by any type of enterprise, organization, or department, such as, for example, providers of healthcare products and/or services responsible for servicing the health and/or welfare of people in its care. For example, the system 200 represents a hospital information system. A healthcare provider may provide services directed to the mental, emotional, or physical well being of a patient. Examples of healthcare providers include a hospital, a nursing home, an assisted living care arrangement, a home health care arrangement, a hospice arrangement, a critical care arrangement, a health care clinic, a physical therapy clinic, a chiropractic clinic, a medical supplier, a pharmacy, and a dental office. When servicing a person in its care, a healthcare provider diagnoses a condition or disease, and recommends a course of treatment to cure the condition, if such treatment exists, or provides preventative healthcare services. Examples of the people being serviced by a healthcare provider include a patient, a resident, a client, and an individual.

Each of the elements in the system 200 may be fixed and/or mobile (i.e., portable), and may be implemented in a variety of forms including, but not limited to, one or more of the following: a personal computer (PC), a desktop computer, a laptop computer, a workstation, a minicomputer, a mainframe, a supercomputer, a network-based device, a personal digital assistant (PDA), a smart card, a cellular telephone, a pager, and a wristwatch. The system 200 may be implemented in a centralized or decentralized configuration.

In the system 200, one or more elements may be implemented in hardware, software, or a combination of both, and may include one or more processors. A processor is a device and/or set of machine-readable instructions for performing task. A processor includes any combination of hardware, firmware, and/or software. A processor acts upon stored and/or received information by computing, manipulating, analyzing, modifying, converting, or transmitting information for use by an executable application or procedure or an information device, and/or by routing the information to an output device. An executable application comprises code or machine readable instruction for implementing predetermined functions including those of an operating system, healthcare information system, or other information processing system, for example, in response user command or input. For example, a processor may use or include the capabilities of a controller or microprocessor.

The elements in the system 200 are interconnected, as shown, using one or more networks 203 (otherwise called a communication path or link). The elements in the system 200 communicate over the network 203 using any type of protocol or data format including, but not limited to, the following: an Internet Protocol (IP), a Transmission Control Protocol Internet protocol (TCPIP), a Hyper Text Transmission Protocol (HTTP), an RS232 protocol, an Ethernet protocol, a Medical Interface Bus (MIB) compatible protocol, a Local Area Network (LAN) protocol, a Wide Area Network (WAN) protocol, a Campus Area Network (CAN) protocol, a Metropolitan Area Network (MAN) protocol, a Home Area Network (HAN) protocol, an Institute Of Electrical And Electronic Engineers (IEEE) bus compatible protocol, a Digital and Imaging Communications (DICOM) protocol, and a Health Level Seven (HL7) protocol.

The system 200 includes an integrated medical database to support the delivery of more efficient and higher quality health care. Information derived from the database is fed back into the health care delivery process for systems to provide more proactive and intelligent assistance to the health professional at the point of care, and is fed back into the analysis and mining process to facilitate the discovery of new knowledge by information analysts.

The system 200 provides a single-source, universal integrated medical database for stakeholder/user access in any enterprise, university, local, regional, or national health market (assuming proper security clearance). Multiple data types from multiple data sources are linked and normalized within persons/patients for easy access to complete information. Persons are additionally linked into other contexts, such as disease cohorts (i.e., diseases having a statistical factor in common). In contrast to the extensive installation effort needed for the typical operational health information system, little effort is required to start accepting data into the integrated medical database. Derived information is integrated back into the health care delivery process through interfaces for models and rules that are fed into the workflow, rules, and vocabulary engines within the local healthcare information systems.

In the context of data mining and data enhancement through data processing, it is common to differentiate between data, information, and knowledge. Although general definitions for these terms are available in various forms, definitions that uniquely and exactly differentiate the meaning of the terms are lacking. Therefore, wherever in the context of this patent application one of the terms data, information, or knowledge is used, these terms are not meant to restrict the scope of the claims herein or the data set addressed. For sake of clarity, in the formulation of the claims the term "information" is used, but it is to be understood that this term covers the complete range of data, information, and knowledge.

The integrated medical database provides "always-on", pay-as-you-go or subscription-paid, discrete application and knowledge services for use and branding by any health information system (HIS) or health portal, whether an independent vendor solution, a proprietary health care provider solution, a government solution, a research system, a non-provider system, or an independent health care consumer, worldwide. The system helps optimize health care workflows, improving the quality and efficiency of the care delivered.

The system 200 advantageously performs the following functions, for example:

1. Collects, integrates, normalizes, stores, and manages many different data types from many different data sources.

2. Provides the tools, techniques, and applications to access the data.

3. Supports information and knowledge modeling to define relationships in the underlying data and the information derived from them.

4. Provides the means to feed the information back into point of care systems to recommend diagnoses and clinical actions, and to predict future behavior and outcomes, and to "back office" information systems to facilitate and validate the derivation of new information, models, and rules, thereby optimizing knowledge discovery.

The system 200 is used advantageously in the following functional areas, for example:

1. Clinical trial support (e.g., patient identification, outcomes analysis).

2. Clinical decisions support (e.g., feature extraction, exemplary cases, differential diagnosis, therapy simulation).

3. Consumer health service (e.g., lifetime record, personalized medicine).

4. Outcome analysis and process optimization (e.g., benchmarking, evidence-based best practice).

The system 200 provides the following advantages, for example, to enable proactive delivery of efficient and effective health and healthcare, as follows:

1. Data of multiple types is collected from multiple points of health care delivery and health care research (including, but not limited to, administrative, clinical, image, financial, and genomic/proteomic data).

2. Data is integrated to create a complete, integrated, and patient-centered medical database. Available person identifiers (e.g., social security number) and genetic data is used to link patient data.

3. Data is separately transformed, enhanced, and stored in structures (data marts) to facilitate data mining, data analysis, and the monitoring of performance metrics.

4. Model and rules, which are derived from both the patterns and relationships discovered through mining and analysis and already established patterns and relationships, create predictive and actionable knowledge.

5. Application functions support clinical decision making by deriving and infusing structured information and evidence-base best practice into health care delivery (e.g., clinical trial support, clinical decision support, personalized medicine, outcome analysis).

6. Data and application functions are accessed through published, standard messaging protocols.

7. Data and application functions are accessed directly by health professionals at any point in health care delivery, and by information analysts in a back room.

8. Data and application functions are accessed directly or through any health information system, any time, anywhere.

9. Data and application functions are optionally packaged into and branded by any health information system.

10. Security and data integrity are tightly integrated and controlled.

Features of the system 200 include, for example, the following:

1. Feeding the derived information, models, and rules back to operational systems, where healthcare process can be optimized at the point of service through tightly coupled rules, workflow, and terminology services.

2. Feeding the derived information, models, and rules back to informational system knowledge stores, where rules and terminology services help facilitate and validate the derivation of new information, models, and rules, thereby optimizing knowledge discovery.

3. Using genetic data to control person identification and data management (e.g., merge person records if genetic profile is the same).

4. Using genetic data to control person access to his/her own data as the central electronic health record.

5. Defining an installation process and tools for new data feeds, where install time in minimized.

6. Defining terms, codes, and identifiers that facilitate the integration of person, clinical, and genetic data.

7. Integrating genetic data into the existing administrative, clinical, and financial data sets, and integrating genetic data into health information system (HIS) applications.

Figure 5:
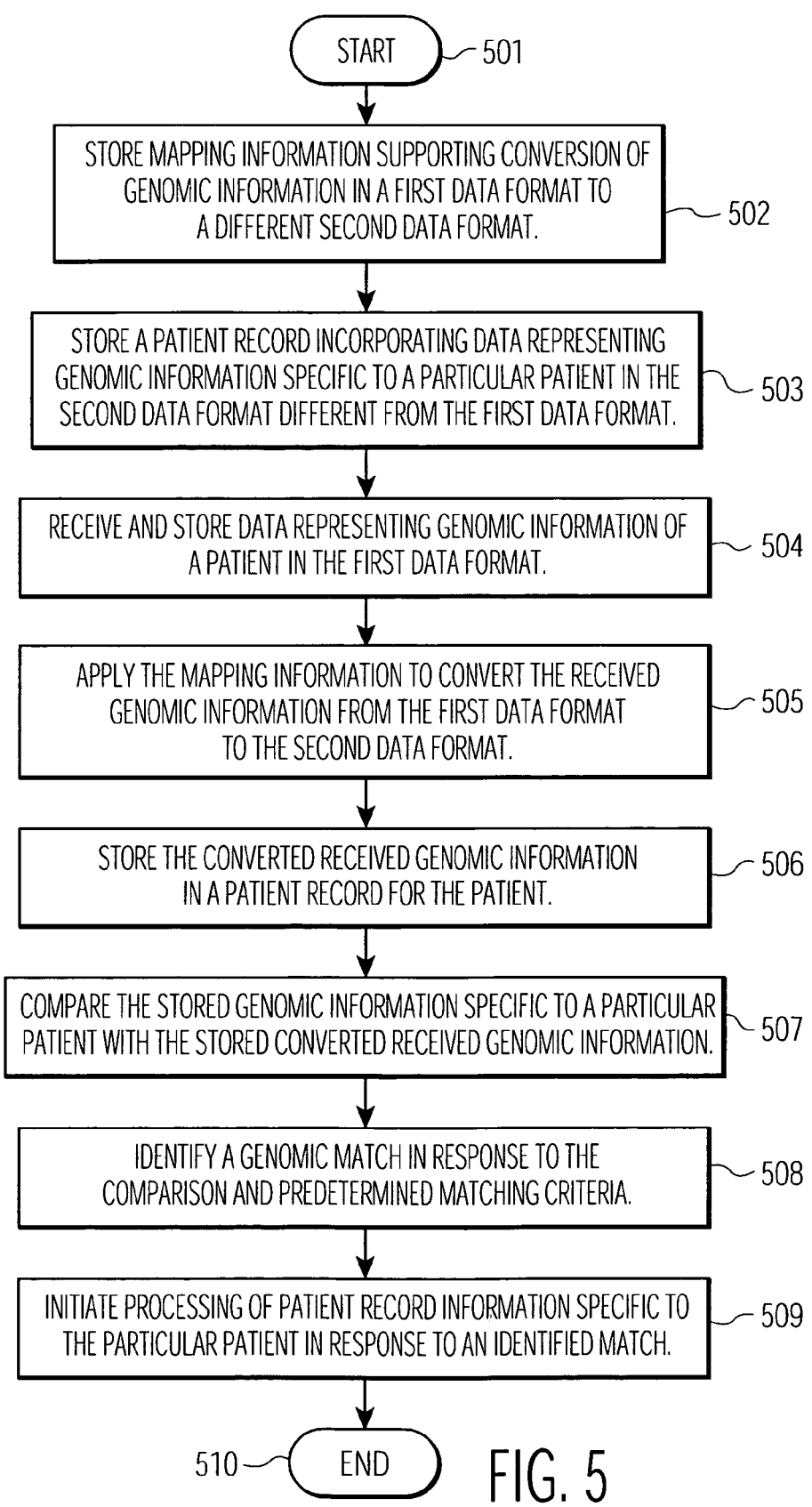
FIG. 5 illustrates a data transformation method for the healthcare system, as shown in FIG. 2, in accordance with invention principles.

8. Using the layered approach to integrated medical data and knowledge modeling as illustrated in FIG. 5.

9. Providing an open, pay-as-you-go, service-enabled function set for accessing integrated medical database capabilities, where a system can plug into and use the environment to enhance their own local capabilities.

A. Information Source/Sink

The information source/sink 202 (otherwise called "data suppliers and information consumers") includes information supplied by any source, and information received by any user or system, including for example, healthcare provider systems. Example of information sources include the following:

1. External knowledge and Benchmark information, which may come from public data sources.

2. Administrative, clinical, and financial data, which may come primarily from healthcare provider information systems.

3. Imaging data, which may come primarily from modality and PACS systems.

4. Non-healthcare provider data, which primarily may come from durable goods suppliers and payers.

5. Genomics and proteomics data, which may come from universities and testing labs.

6. Clinical trials data, which may come from clinical trial systems (clinical trials data is no different than other types of clinical and administrative data, but are different in terms of functions they support).

B. Data Interface Processor.

The data interface processor 204 receives data, transactions and files from the information source 202, and sends data, transactions and files to information sink 202. The data interface processor 204 provides functions, including for example, protocol and data conversions, routing, queuing, and error handling. The rules for transaction parsing and processing are maintained in an associated interface catalog (not shown in the system 200). Standard interface protocols are supported (e.g., HL7, DICOM, X12N, MAGE, and CDISC, as shown in FIG. 2), but non-standard protocols are also accommodated. Many different transaction formats exist in the health industry, and it is the responsibility of the data interface to collect and transform transactions to a format acceptable for the data update processor 206, which updates the health data repository 208. The data interface processor 204 also supports the initial back load of person and clinical data from existing enterprise repositories as part of the initial install of a new data supplier site.

C. Data Update Processor

The data update processor 206 receives transactions from the data interface processor 204 and updates the health data repository 208. The data update processor 206 understands the transaction formats and target data model, and provides the business logic that defines how data is to be inserted into the data model.

D. Health Data Repository

Figure 3:
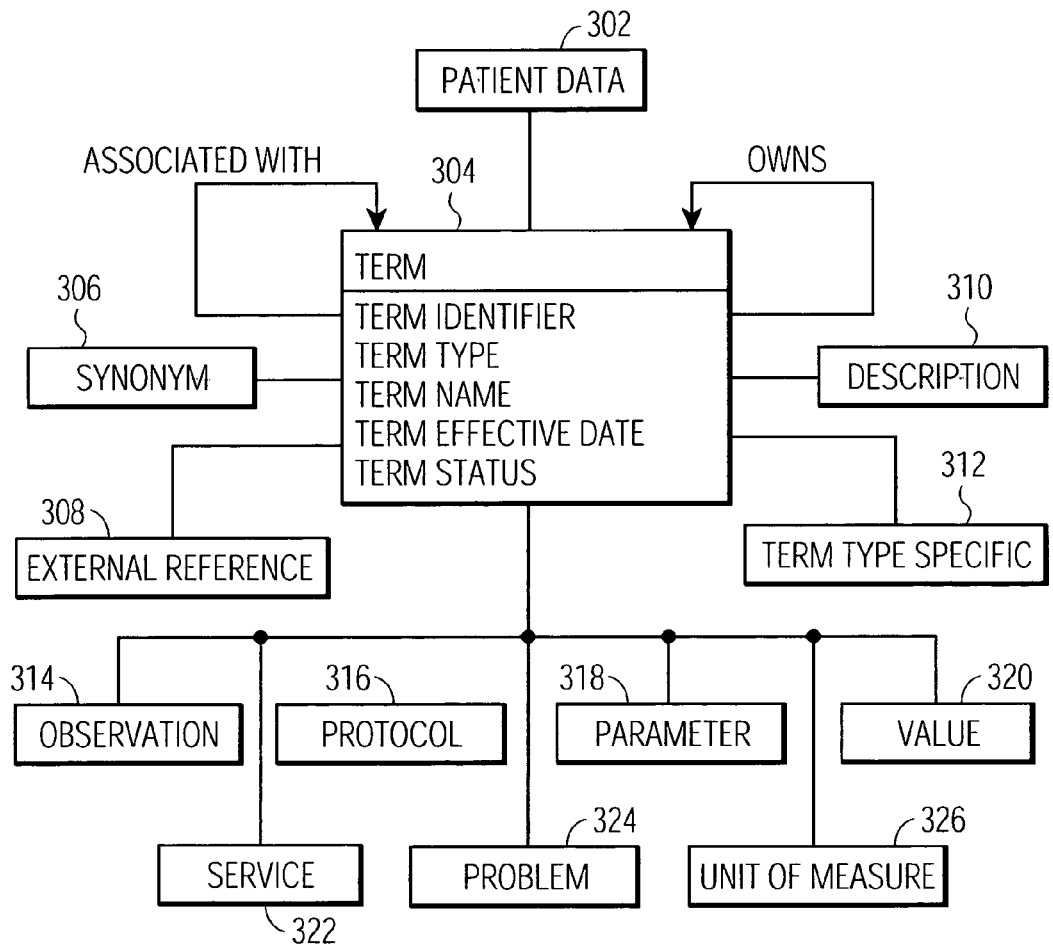
FIG. 3 illustrates a repository storage model for a health data repository in the healthcare system, as shown in FIG. 2, in accordance with invention principles.

FIG. 3 illustrates a repository storage model 300 for health data repository 208 in the healthcare system, as shown in FIG. 2. The health data repository 208 represents a data storage element and may include a storage device, a database, a memory device, cache, etc. The health data repository 208 supports a single patient-centered data storage facility, which can also be accessed for single patient data display. Alternatively, multiple data storage facilities and/or multiple patient data display may be used. The health data repository 208 contains and integrates data collected from external data sources (e.g., person, administrative, clinical, financial, genomic/proteomic, and clinical trial, etc.), linking them to a person identifier and to the encounter in which the data apply. To maintain consistency with the source systems, data is stored in essentially the form in which they are received. The system 200 employs predetermined rules for determining how and where data is deployed, whether in a single physical data store or a distributed data store.

Genomic and/or proteomic data is associated with a person, and is stored in a model consistent with a standard, such as the MAGE-OM standard available on the Internet and from other sources, which aims to provide a standard for the representation of micro-array expression data that facilitates the exchange of micro-way information between different data systems.

The repository storage model 300 is a flexible and extensible meta-model, which is necessary to assimilate current and future data. For example, detailed clinical data is linked to a person and encounter, and are stored in a generic structure, as shown in FIG. 3.

In FIG. 3, the patient data 302 contains a complete description of a record associated with a patient (characteristics, demographics, etc.). The term 304 defines a unit of clinical data in the patient record, represented by, for example, identifier, type, name, effective date, and status. Elements 306 to 326 identifies various aspects of the terms 304, including data attributes relevant to each term. Synonym 306 identifies the multiple ways a single clinical concept may be described. External reference 308 points to equivalent terms in other terminologies, as well as supportive details stored in external data stores such as details of a drug. Description 310 provides the detail description of a term. Term type specific 312 contains data extending a term based on the type of term. Observation 314 is clinical data such as a lab result, radiology report, patient assessment, etc. Protocol 316 is a set of actions to be taken in the care of a disease or combination of diseases. Parameter 318 describes information such as duration and frequency of a service. Value 320 describes the actual numeric or text values, normal ranges, etc. Service 322 is an action taken such as a medication, physical therapy, vaccination, etc. Problem 324 describes the reasons for care such as sign, symptom, diagnosis, etc. Unit of measure 326 describes information such as milliliters, centimeters, inches, etc.

E. Data Transform Processor

Figure 4:
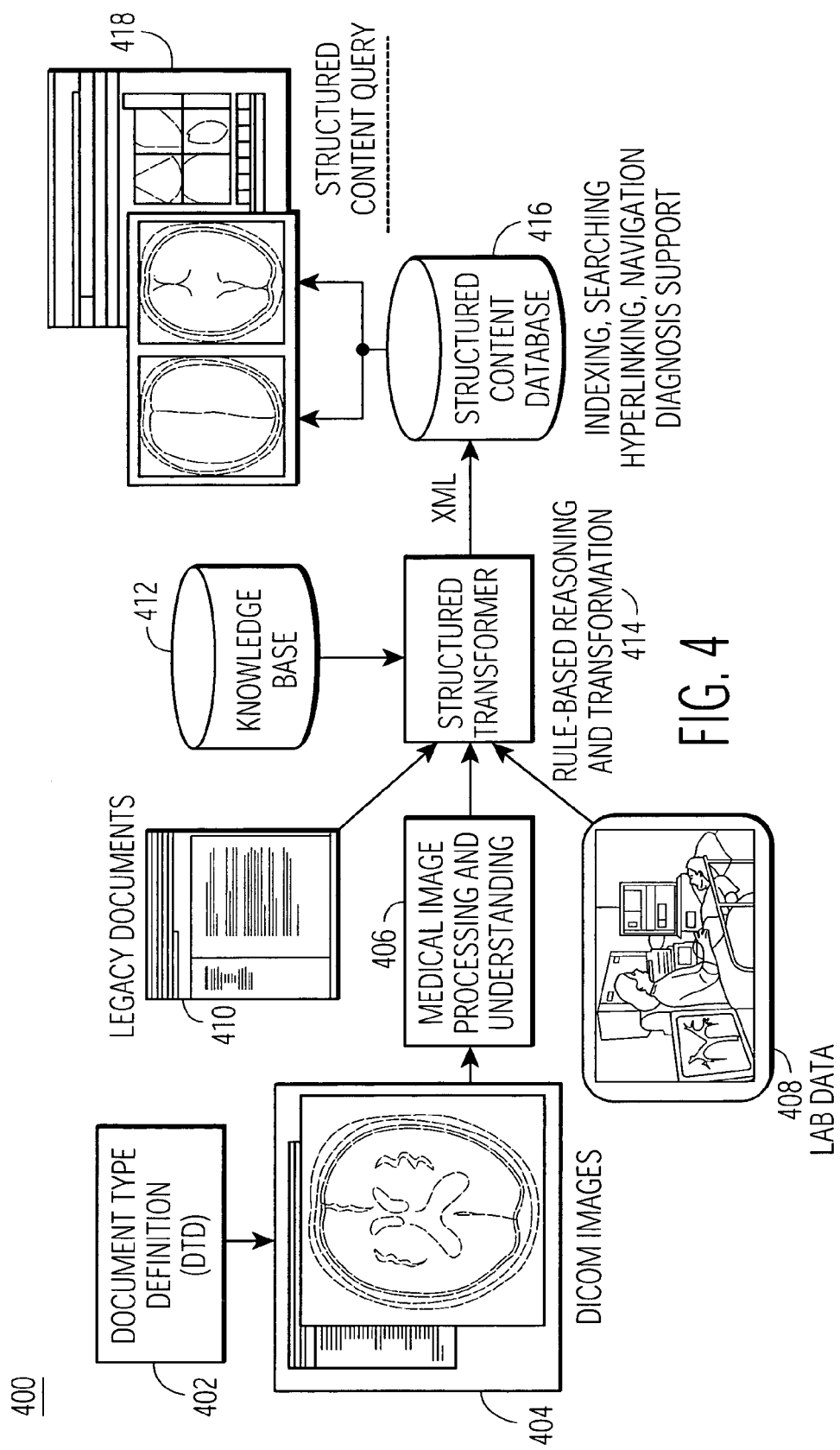
FIG. 4 illustrates a data transformation processor for the healthcare system, as shown in FIG. 2, in accordance with invention principles.

FIG. 4 illustrates a data transform processor 210 as part of a data transformation system 400 for the healthcare system 200, as shown in FIG. 2. The data transformation system 400 may transform any type of healthcare information including, for example, image data, genomic and/or proteomic information, document data, and lab data. The data transformation system 400 provides automated transformation from a first data format (e.g., unstructured data) to a second data format (e.g., structured data). The data transformation system 400 also provides template specifications and XML-based data capturing (e.g., HL7/XML template processing). Since relevant medical image content is context-dependent, a priori information is needed to determine what is relevant in the image data.

The data transformation system 400 includes document type definitions (DTD) 402, DICOM images 404, a medical image processing and understanding processor 406, lab data 408, legacy documents 410, a knowledge base storage device 412, a structured transformer processor 414, a structured content database 416, and a user interface 418. The structured transformer processor 414, representing the data transform processor 210, provides rule-based reasoning and transformation. The structured content database 416 provides indexing, searching, hyper-linking, navigation, and diagnosis support. The user interface 418 provides structured content query.

The data transform processor 210 (see FIG. 2) transfers and reconfigures the data from the health data repository 208 into a mining, analysis, and reporting environment, which is called data warehousing 212 in the system 200. The data in the health data repository 208 is not directly usable (at least without sophisticated data processing tools) for mining purposes, and needs to be converted to another format and structure for more practical access. For example, content structuring occurs by taking the features extracted from images and text documents, other structured clinical and patient data, and models and rules defined through knowledge/information modeling processor 222 described below, and applying rules-based reasoning and transformation to create structured content, typically in extensible markup language (XML) form.

The data transform processor 210 and/or the data interface processor 204 also authorizes access by a user to a patient record of a particular patient in response to an identified match, and/or authorizes access by a particular patient to his or her own patient record in response to an identified match.

Access to data at its source is an alternative to integrating data from all sources into a single physical repository. Typically, some combination of distributed and centralized access is used to implement the system 200.

FIG. 5 illustrates a data transformation method 500 performed by the data transform processor 210 and other elements in the healthcare system 200, as shown in FIG. 2. The method 500 may be performed with any number or combination of appropriate steps. Hence, appropriate sub-combinations of steps of the method 500 may be performed, without performing each step of the method. The method processes genomic information, but may also process proteomics information, or any other type of healthcare information.

Genomic healthcare is healthcare that utilizes advances made by the science of genomics. Genomics is a branch of biotechnology concerned with applying the techniques of genetics and molecular biology to the genetic mapping and DNA sequencing of sets of genes or the complete genomes of selected organisms using high-speed methods, with organizing the results in databases, and with applications of the data (as in medicine or biology).

Genomics is the study of genes and their function. Recent advances in genomics are bringing about a revolution in our understanding of the molecular mechanisms of disease, including the complex interplay of genetic and environmental factors. Genomics is also stimulating the discovery of breakthrough healthcare products by revealing thousands of new biological targets for the development of drugs, and by giving scientists innovative ways to design new drugs, vaccines and DNA diagnostics. Genomics-based therapeutics includes traditional small chemical drugs, protein drugs, and potentially gene therapy.

Genomic information comprises, for example, at least one of the following: (a) DNA information, (b) RNA information, (c) complementary DNA or RNA information, (d) transfer RNA (tRNA) information, (e) messenger RNA (mRNA) information, and (f) Expressed Sequence Tags (EST).

Genome is the genetic material in the chromosomes of a particular organism; its size is generally given as its total number of base pairs. Genomic DNA is the basic chromosome set consisting of a species-specific number of linkage groups and the genes contained therein. A genomic library is a collection of clones made from a set of randomly generated overlapping DNA fragments representing the entire genome of an organism. Genetic testing is performed to gather information on an individual's genetic predisposition to particular health condition, or to confirm a diagnosis of genetic disease, for example.

Proteomics is a branch of biotechnology concerned with applying the techniques of molecular biology, biochemistry, and genetics to analyzing the structure, function, and interactions of the proteins produced by the genes of a particular cell, tissue, or organism, with organizing the information in databases, and with applications of the data (as in medicine or biology).

At step 501, the method 500 starts.

At step 502, the method 500 stores mapping information (otherwise called "common elements") supporting conversion of genomic information in a first data format to a different second data format. Mapping information includes, for example, at least one of the following: (a) codes (or code sets), (b) terms, and (c) identifiers derived from multiple different sources and supporting interpretation of genomic information derived from different sources.

The codes, terms, and identifiers include HIPAA (Health Information Portability and Accountability Act) compatible code sets and other code sets used in a health care operation. Such code sets include, for example, ICD (International Classification of Diseases) codes, 9th Edition, Clinical Modification, (ICD-9-CM), Volumes 1, 2 and 3, as well as ICD-10 maintained and distributed by the U.S. Health and Human Services department. The code sets also include code sets compatible with HCPCS (Health Care Financing Administration Common Procedure Coding System), NDC (National Drug Codes), CPT-4 (Current Procedural Terminology), Fourth Edition CDPN (Code on Dental Procedures and Nomenclature). Further the code sets and terms include code sets compatible with SNOMED-RT "Systematicized Nomenclature of Medicine, Reference Terminology" by the College of American Pathologists, UMLS (Unified Medical Language System), by the National Library of Medicine, LOINC Logical Observation Identifiers, Names, and Codes Regenstrief Institute and the Logical Observation Identifiers Names and Codes (LOINC(r)) Committee, Clinical Terms also known as "Read Codes", DIN Drug Identification Numbers, Reimbursement Classifications including DRGs Diagnosis Related Groups. The code sets also include code sets compatible with CDT Current Dental Terminology, NIC (Nursing intervention codes) and Commercial Vocabulary Services (such as HealthLanguage by HealthLanguage Inc., by Apelon Inc.) and other code sets used in healthcare.

The terminology, including vocabularies, code sets, and identifiers, is employed in characterizing or identifying a health provider organization, a location in an organization, a healthcare worker, a medical condition, a health service, a cost of a medical procedure or service, a payer organization, or a particular health plan. The health data repository 208 and/or the data warehouse 212 contains medical terms, vocabularies and identifiers in addition to organizational characteristics, as well as location and other information supporting identification of location availability and suitability in a particular organization for delivering services by a particular physician to a patient with a particular medical condition. A medical code set as used herein is any set of codes used for encoding data elements, such as tables of terms, medical concepts, medical diagnosis codes, or medical procedure codes.

At step 503, the method 500 stores a patient record incorporating data representing genomic information specific to a particular patient in the second data format different from the first data format.

At step 504, the method 500 receives and stores data representing genomic information of a patient in the first data format.

At step 505, the method 500 applies the mapping information to convert the received genomic information from the first data format to the second data format.

At step 506, the method 500 stores the converted received genomic information in a patient record for the patient.

At step 507, the method 500 compares the stored genomic information specific to a particular patient with the stored converted received genomic information.

At step 508, the method 500 identifies a genomic match in response to the comparison and predetermined matching criteria.

At step 509, the method 500 initiates processing of patient record information specific to the particular patient in response to an identified match. The method 500 may initiate merging of at least a portion of the patient record information specific to the particular patient with another patient record in response to the identified match. The method 500 may identify a second patient record replicating patient record information specific to the particular patient in response to the identified match.

At step 510, the method 500 ends.

F. Data Warehouse/Data Marts.

Figure 6:
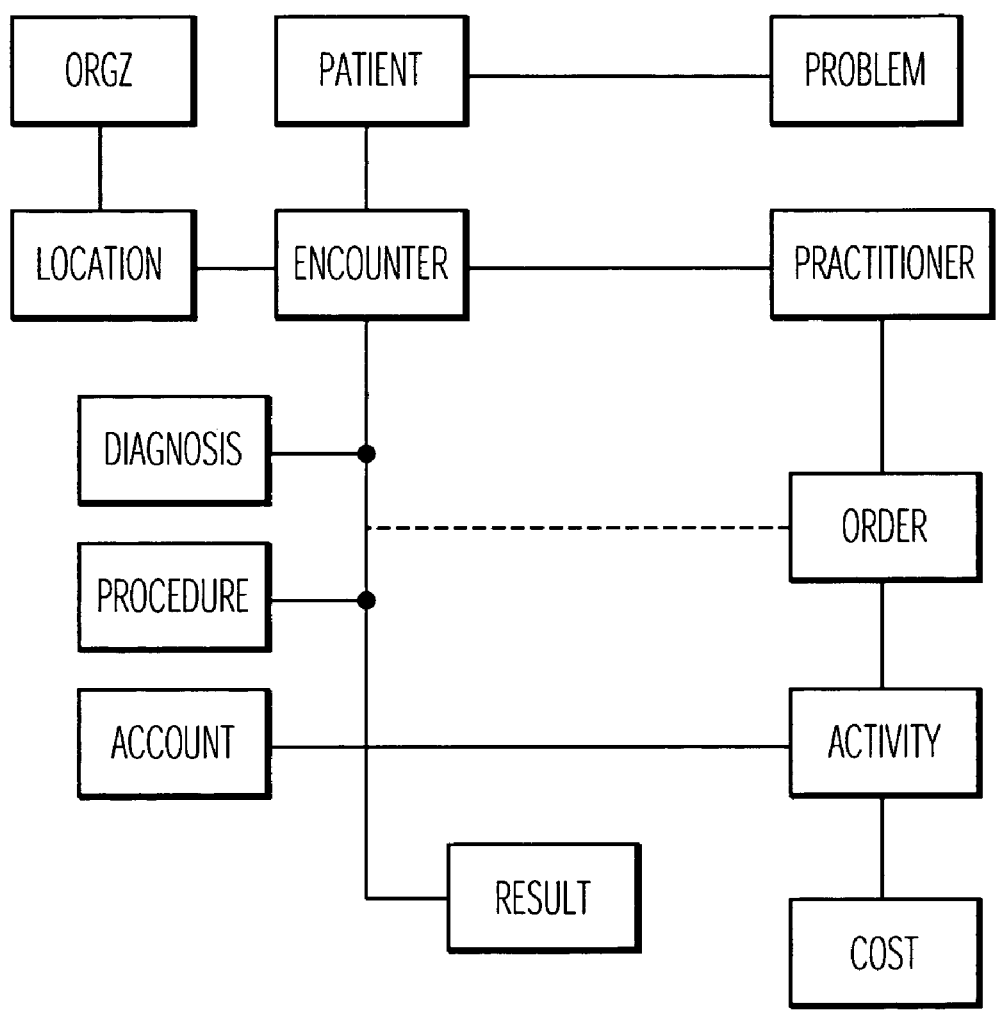
FIG. 6 illustrates a data warehouse storage model for a data warehouse in the healthcare system, as shown in FIG. 2, in accordance with invention principles.

FIG. 6 illustrates an example of a data warehouse storage model 600 for the data warehouse 212 in the healthcare system, as shown in FIG. 2. The data warehouse storage model 600 supports cross patient data analysis and mining, but can also support single patient access. Instead of the more flexible and extensible meta-structures associated with the health data repository 208, data is stored in structured relational form, which can be used more directly and easily. Specific objects (e.g., person, patient, encounter, order, diagnosis, result, service) and their relationships are defined.

Specialized cohorts or data marts (e.g., by disease, by market, etc.) are constructed from the main warehouse database, or directly from the health data repository 208. The warehousing environment provides both the tools necessary to normalize, transform, and manage data within the data warehousing environment, and the underlying structured data model into which data is stored.

The data warehouse 212 is used for storing, manipulating, and managing data for analysis purposes. Typically, topic-specific data marts are created using native data warehousing tools, or in some cases are created directly during the transformation process. Data enhancement is also done as part of the transformation process. New data is derived from existing data and physically added to the database (e.g., totaling numeric data, categorizing of detailed data into more general groups, assigning diagnosis related groups). For more complex, commonly needed derivations, the data warehouse 212 provides a more efficient resource than re-deriving new results for each new information request.

G. Data Service Processor

The data service processor 214 (see FIG. 2) provides some important functions necessary to manage the data in the health data repository 208 and the data warehouse 212, described as follows.

1. Vocabulary services define the allowable data to be stored in data stores, define the relationships between objects and between clinical concepts, and provide services to define the mapping of source data components and values to standard system objects and terms. The installation effort to define the terms for a new data source and their mapping to internal terms is significant. To help minimize this effort, some aspects of the underlying terminology are defined dynamically as the data is received, avoiding some install effort, and some are predefined as a reference terminology into which interfaced terminologies integrate.

2. Patient identification services are needed to determine the person's unique identifier in the health data repository 208 for new incoming data. Patient identifiers (e.g., social security number, medical record number) in the incoming data is used directly, or probabilistic matching is used to identify the patient and the associated patient identifier from descriptive data provided in the incoming data stream, or the genomic and/or proteomic data is used to identify and match person data. Other services include person, and data management functions (e.g., merge and unmerge persons) in the databases. The underlying person index contains the complete person census relevant for the scope of the geographic install and system operation.

3. Patient de-identification and anonymization occurs to comply with privacy rules, which dictate that patients' protected health information not be identifiable if it is transmitted outside of the provider environment, unless explicit patient permission is granted for broader data use. Standard algorithms are used to assign fake names and to otherwise make the data and patient anonymous (e.g., change any data that could potentially be used to indirectly identify a person). De-identification may be performed by the data interface processor 204 or by the information source 202, before data is permanently recorded in the main databases. Alternatively, de-identification may also be done at other points in the process if it is desired to maintain patient identifying data in the main repositories, but to de-identify it for subsequent information processing use. When the system is used in personalized medicine, it may be necessary for the patient data to be tied to a real person. Meaningless identifiers may be used within the repositories, but a link/key be maintained to ultimately be able to tie the data to a specific individual.

4. An audit provides the services to record and trace updates and accesses to the system, and to also provide links back to the original data sources. Audit records are stored in a separate common repository not shown in the system 200. A standard protocol is used to communicate audit events to the health data repository 208.

5. Content Extraction.

Figure 7:
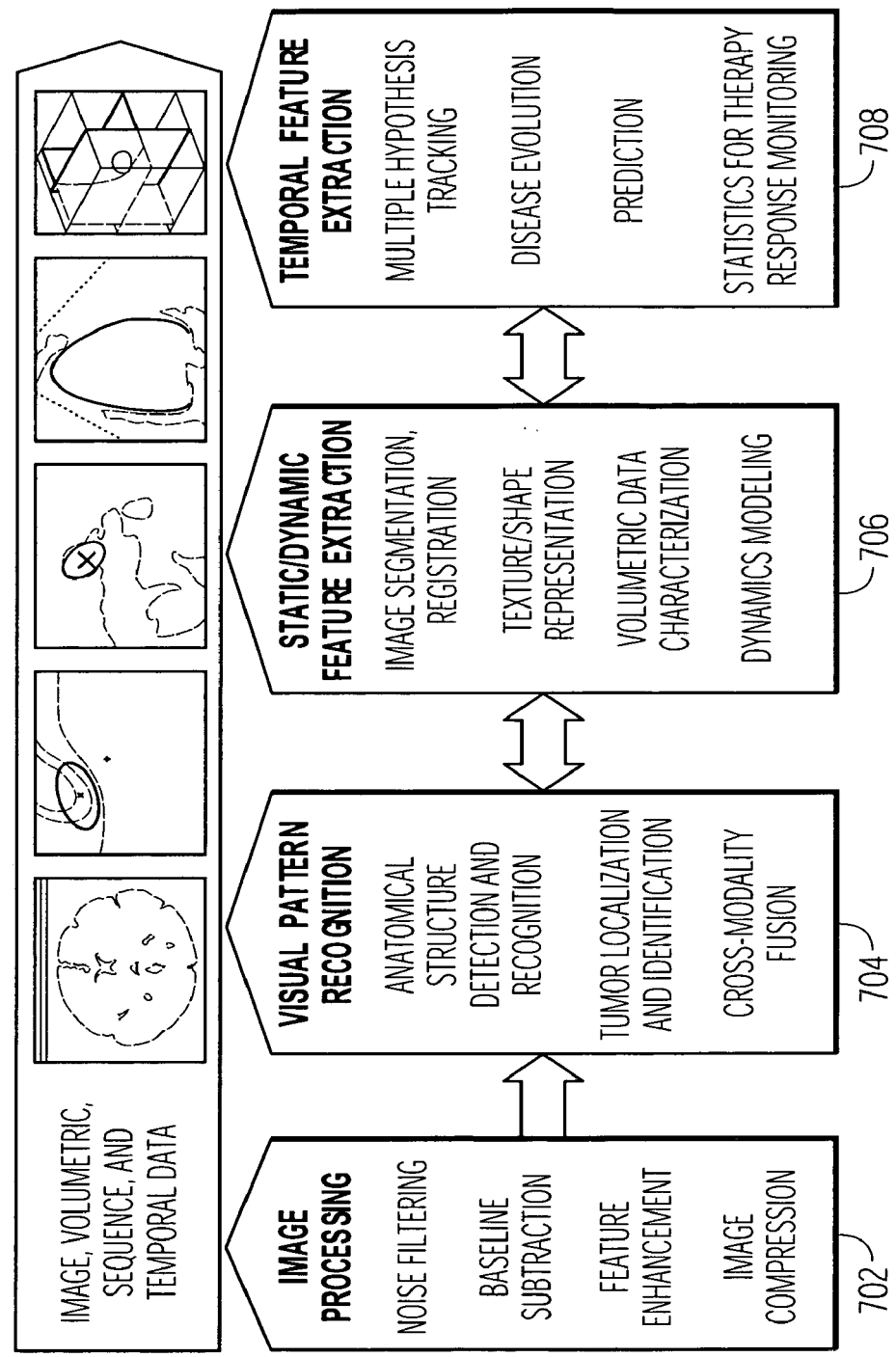
FIG. 7 illustrates a medical image process model for the healthcare system, as shown in FIG. 2, in accordance with invention principles.

FIG. 7 illustrates a medical image process model 700 for the healthcare system 200, as shown in FIG. 2. Unstructured data, such as images and text documents, are analyzed and important features are extracted and structured for subsequent use. Image processing and understanding algorithms are employed in content extraction. Such algorithms include image processing 702 (noise filtering, baseline subtraction, feature enhancement, image compressions), visual pattern recognition 704 (anatomical detection and recognition, tumor localization and identification, cross-modality fusion), static/dynamic feature extraction 706 (image segmentation registration, texture/shape representation, volumetric data characterization, dynamics modeling), and temporal feature extraction 708 (multiple hypothesis tracking, disease evolution, prediction, statistics for therapy response monitoring). For example, heart measurements are extracted from heart images. Ideally, the medical image process model 700 is autonomous, real-time, consistent, un-biased, and validated.

6. Data Quality. Other than the usual, physical, and logical edits on the incoming data, probabilistic inference is necessary for handling missing or inconsistent data. In addition, where possible, balancing and other forms of cross-data consistency checking are performed to assure overall completeness and data integrity.

H. Data Mining and Analysis Processors

The data mining and analysis processors 216 are used to create information about the large quantities of unstructured and structured data in the repositories.

1. A data mining processor is used to discover new structures in the data (i.e., knowledge discovery), by searching for and identifying new and valid patterns and relationships within them. Basic tool sets and healthcare-specific algorithms are provided for direct, ad hoc use against the data stores, and are structured and packaged for ease of use to address more commonly studied areas.

2. A data analysis processor provides simple reports (e.g., listings, charts, graphs) through report writers, online analytical processing (OLAP) function through database formats, such as star schemas and "cubes," and statistical functions to test hypotheses and validate relationships.

I. Applications

The applications 218 represent packaged functions and/or solutions that hide and organize the complexities of the underlying repositories, and provide ongoing function to knowledge professionals and health professionals. The underlying technology infrastructure 228 provides a set of common functions, common engines, and other common applications to facilitate the building of new applications. These applications have their own user interfaces, but are also service-enabled to expose application-programming interfaces (APIs) for external system use. Examples of application areas include:

1. Performance management (e.g., executive information systems, where performance metrics are derived and reported in the context of acceptable thresholds, and variances from expected ranges are reported to appropriate parties).

2. Clinical trial support (e.g., patient identification, trials management, outcomes analysis).

3. Clinical decision support (feature extraction, therapy simulations, differential diagnosis functions, selection of exemplar patients).

4. Consumer health service (e.g., lifetime record, personalized medicine).

5. Outcome analysis and process (e.g., benchmarking, evidence-based best practice).

J. Feedback Processor

The feedback processor 220 enables significant information derived by information analysts, which are organized and structured into standard formats, to be fed back to workflow, rules, and vocabulary engines in the operational systems, and to be fed back into the integrated medical database domain itself. In this fashion, both point of care and innovation processes are optimized. Standard interface protocols are used to transfer this information between systems.

K. Knowledge/Information Modeling Processor.

Figure 8:
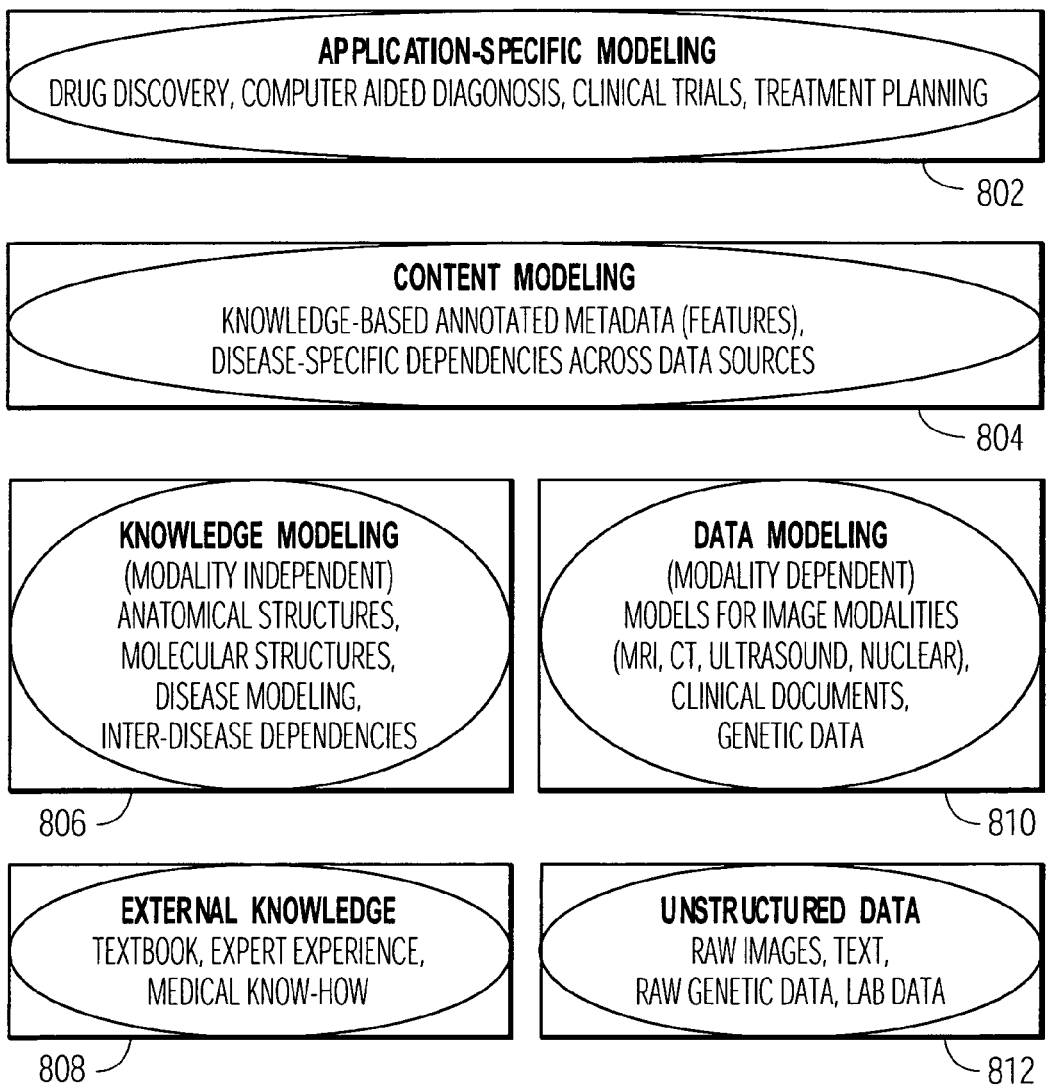
FIG. 8 illustrates a medical data and knowledge model for the healthcare system, as shown in FIG. 2, in accordance with invention principles.

FIG. 8 illustrates a medical data and knowledge model 800 for the modeling processor 222 in the healthcare system, as shown in FIG. 2. The modeling process involves using external knowledge 808 (e.g., from published papers, text books) that describes known patterns and relationships 806 (e.g., anatomical structures, molecular structures). The modeling process also involves data modeling 810 derived from patterns and relationships from the mining, analysis, and metrics information of unstructured data 812. The knowledge modeling 806 is integrated with the data modeling 810 to create content modeling 804 (e.g., new models and rules) that help to provide application-specific modeling 802 (e.g., recommend diagnoses and actions, and predict behavior and outcomes). The content modeling 804 are stored in a models/rules knowledge base 223, which in turn are used by other functions and applications. The embedding of these derived models and rules in both the operational and informational systems provide advantageous healthcare delivery.

L. User Interface

Besides accessing functions and applications within the bounds of the integrated medical database, a single user, acting in a particular role at a particular workplace, potentially needs to access function from multiple systems within a single workflow. The user interface 224 provides the means for a user to initiate and manage a single session that includes, for example, diverse and separate products, applications, and functions, and to share patient context across them. Capabilities include cache management, linking patient data, and generating messages following SOAP and XML protocols.

1. Session management provides the means to share the context of a single user across multiple applications (e.g., timeouts, automatic logoff). Each application does not have to identify or manage the end user session. This is accomplished by the parent application of the session.
2. Context management provides the services to share the context of single patient. Each application does not have to re-identify a patient and associated information.
3. Security provides the services to manage role-based access to the environment for end users (e.g., identification, authentication, authorization). They support the authorization (authentication, access control), asset protection (secure communications, data storage, and keys), accountability (logging of system and data access), administration (centralized management and single point of maintenance), and assurance (boundary protection, intrusion detection, and virus detection).
4. Messaging services support the interactive communication with System functions and with external front-end HIS systems. Service requests in the form of messages are passed through APIs to feed data to, and receive data from, the requested data and application services. The functions use the data retrieved to drive their own displays, rules, and/or other business logic. The services are stateless, fast, and highly available, and support synchronous and asynchronous queries, self-defining data streams, standard message data protocols (e.g., SOAP), and metadata, if appropriate (e.g., edit rules, display characteristics, value sets, branching rules). Messaging supports the need to perform service calls (remote procedure calls) to execute functions of a diverse and distributed application set (e.g., managing the list of subscribing services and routing the function call appropriately). External system can synchronously connect to the functions of the system 200 by using the exposed APIs that represent its set of services.

The user interface 224 permits a user to interact with the system 200 by inputting user interface data into the system 200 via a data input device (not shown) and/or receiving user interface data from the system 200, via a data output device (not shown). The user interface 224 generates one or more display images using a display processor (not shown). The display processor generates display data, representing one or more images for display, in response to receiving the input data or other data from the system 200. The display processor is a known element including electronic circuitry or software or a combination of both for generating display images or portions thereof.

M. Subscription/Accounting Processor

The subscription/accounting processor 226 provides subscription services and accounting services. Subscription services support the enrollment of stakeholders/users (e.g., vendors, providers, knowledge users, and consumers) in the system 200, and the ongoing maintenance of their specific profile information, which is needed to control processing. Identification data (e.g., demographics, identifiers, access certificate), authorization and consent for data use, rules for transaction processing (e.g., patient identifier precedence, correction rules, special formats), and rules for data access (e.g., special formats) are defined and maintained. Accounting services support the recording, storage, and processing of activity as necessary to drive usage-based customer pricing and invoicing.

N. Technology Infrastructure

The technology infrastructure 228 contains the basic commodity technologies necessary to drive an IT system (e.g., operating system, database management, middleware, systems management, security, etc.).

Figure 9:
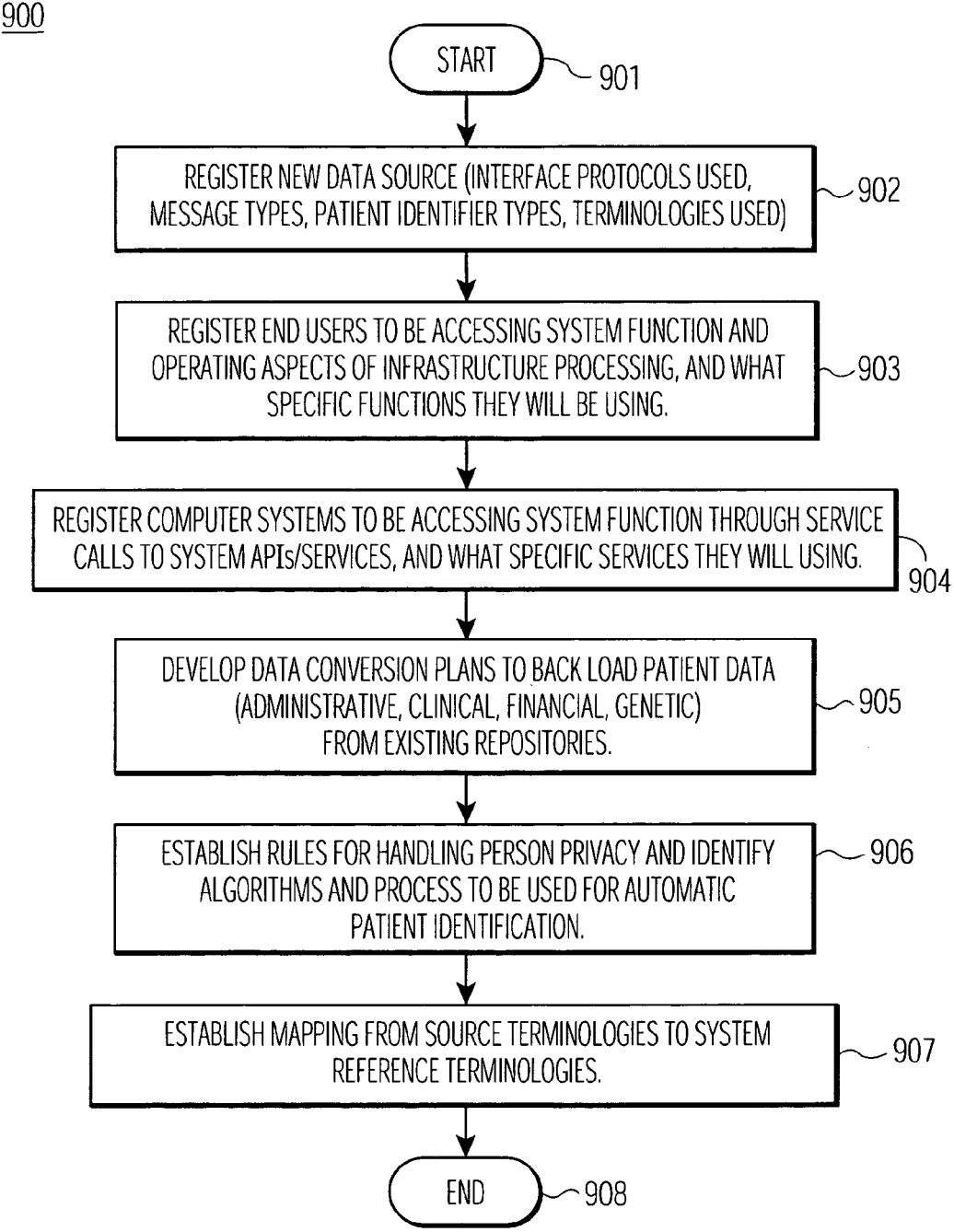
FIG. 9 illustrates an installation method for the healthcare system, as shown in FIG. 2, in accordance with invention principles.

FIG. 9 illustrates an installation method 900 for the healthcare system 200, as shown in FIG. 2.

At step 901, the method 900 starts.

At step 902, the method 900 registers new data sources (e.g., interface protocols used, message types, patient identifier types, terminologies used).

At step 903, the method 900 registers end users to be accessing system function and operating aspects of infrastructure processing, and what specific functions they will be using.

At step 904, the method 900 registers computer systems to be accessing system function through service calls to system application programming interfaces (APIs)/services, and what specific services they will be using.

At step 905, the method 900 develops data conversion plans to back load patient data (e.g., administrative, clinical, financial, genetic) from existing repositories.

At step 906, the method 900 establishes rules for handling a person's privacy, and identifies algorithms and process to be used for automatic patient identification.

At step 907, the method 900 establishes mapping from source terminologies to system reference terminologies.

At step 908, the method 900 ends.

Figure 10:
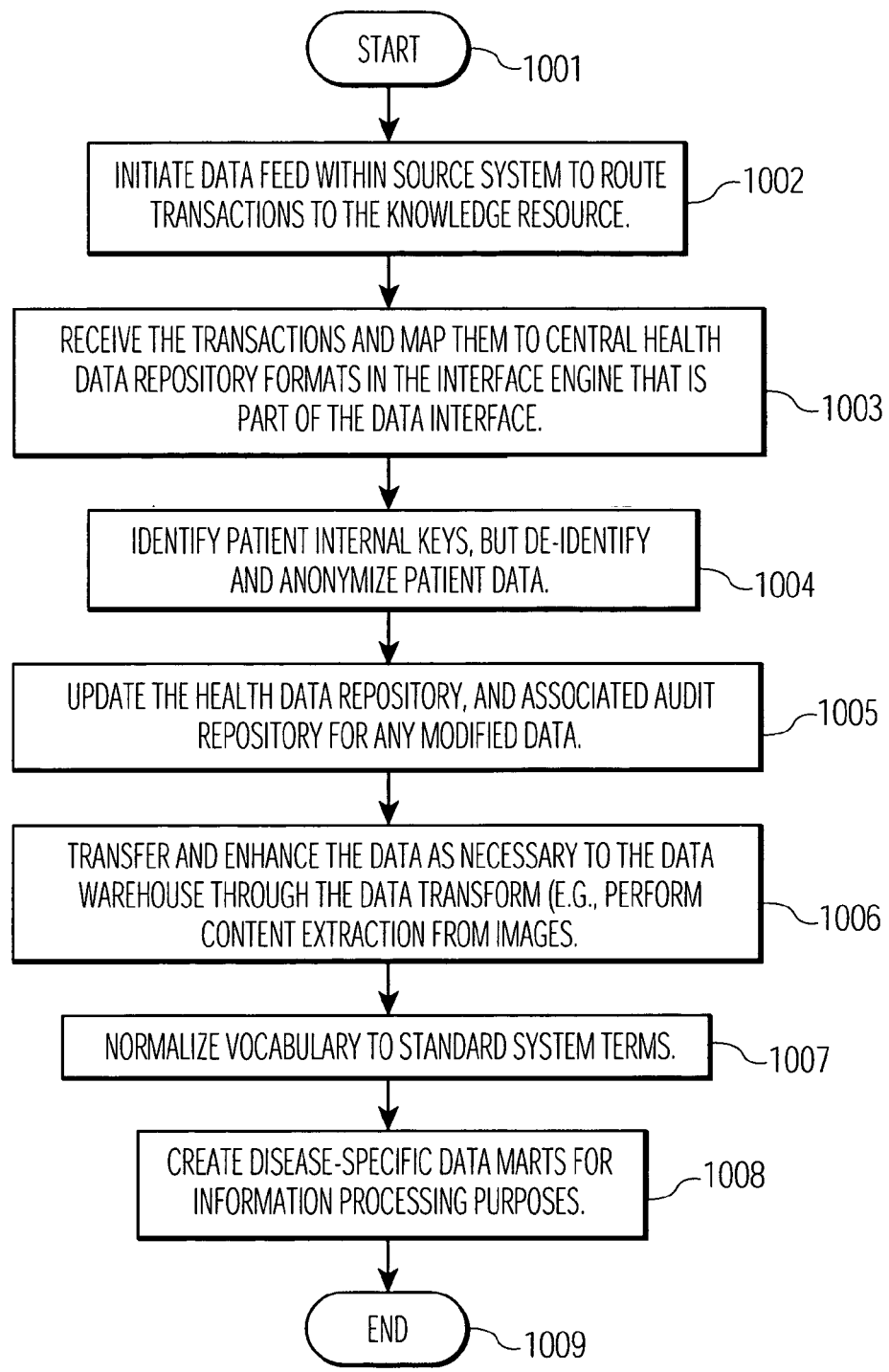
FIG. 10 illustrates a data collection and management method for the healthcare system, as shown in FIG. 2, in accordance with invention principles.

FIG. 10 illustrates a data collection and management method 1000 for the healthcare system 200, as shown in FIG. 2.

At step 1001, the method 1000 starts.

At step 1002, the method 1000 initiates a data feed within the source system to route transactions to the knowledge source.

At step 1003, the method 1000 receives the transactions and map them to central healthcare repository formats in the interface engine that is part of the data interface.

At step 1004, the method 1000 identifies patient internal keys, but de-identifies and anonymizes patient data.

At step 1005, the method 1000 updates the health data repository, and associated audit repository in response to modification of data.

At step 1006, the method 1000 transfers and enhances the data as necessary to the data warehouse through the data transform (e.g., perform content extraction from images).

At step 1007, the method 1000 normalizes vocabulary to standard system terms.

At step 1008, the method 1000 creates disease-specific data marts for information processing purposes.

At step 1009, the method 1000 ends.

FIG. 11 illustrates a data mining and modeling method 1100 for the healthcare system 200, as shown in FIG. 2.

At step 1101, the method 1100 starts.

At step 1102, the method 1100 explores general content of a disease-specific data mart with simple reporting tools to understand general content of the data mart (e.g., patient listings).

At step 1103, the method 1100 uses an OLAP tool to help understand some of the basic performance characteristics of the patients and relationships between dependent and independent variables.

At step 1104, the method 1100 uses mining tools in the context of the constraints, after some of the basic characteristics and assumptions about the data are understood.

At step 1105, the method 1100 searches for new relationships to help optimize healthcare delivery and to predict patient behavior and outcomes.

At step 1106, the method 1100 sets up performance metrics to be monitored on a routine basis, including thresholds of appropriate variation.

At step 1107, the method 1100 combines derived internal information and establishes external knowledge into models and rules that help predict and direct future behavior.

At step 1108, the method 1100 applies the models and rules to the processes of healthcare delivery and clinical research, to help optimize their efficiency and quality.

At step 1109, the method 1100 ends.

Hence, while the present invention has been described with reference to various illustrative embodiments thereof, the present invention is not intended that the invention be limited to these specific embodiments. Those skilled in the art will recognize that variations, modifications, and combinations of the disclosed subject matter can be made without departing from the spirit and scope of the invention as set forth in the appended claims.

What is claimed is:

1. A system for processing patient medical information for storage in an electronic patient medical record repository and suitable for use in a hospital information system, comprising:
   an interface for receiving electronic transaction data including data representing genomic information indicating identity of a first patient, the received genomic information being associated with medical data of said first patient;
   a repository including a record of a particular patient incorporating medical data and data representing genomic information indicating identity of said particular patient; and
   a data processor, electronically coupled to said interface and said repository, for,
      comparing said genomic information indicating identity of said particular patient with the received genomic information associated with medical data of said first patient,
      automatically identifying a genomic match indicating said first patient and said particular patient are the same patient in response to the comparison and predetermined matching criteria, and
   initiating storage of said medical data of said first patient in said record of said particular patient in response to said genomic match and merging of at least a portion of said record of said particular patient with another record of said particular patient in response to said genomic match and using terms, codes, or identifiers that are predefined in the system and that facilitate the integration of clinical and genetic data, to provide a merged record.

2. A system according to claim 1, wherein
said data processor integrates genetic data with existing administrative, clinical, and financial data sets,
said electronic transaction data comprises at least one of, (a) an HL7 compatible message and (b) a DICOM compatible message and
said data processor authorizes access by a user to said record of said particular patient in response to said genomic match.

3. A system according to claim 1, wherein
said data processor authorizes access by said particular patient to his or her own record in response to said genomic match.

4. A system according to claim 1, wherein
said data processor identifies a second record of said particular patient replicating information in said record of said particular patient in response to said genomic match.

5. A system according to claim 1, wherein
said genomic information comprises at least one of, (a) DNA information, (b) RNA information, (c) complementary DNA or RNA information, (d) transfer RNA (tRNA) information (e) messenger RNA (mRNA) information, and (f) Expressed Sequence Tags (EST).

6. A system according to claim 1, wherein
said electronic transaction data is an HL7 compatible transaction and said genomic information is associated with medical data of said first patient in said HL7 compatible transaction.

7. A system according to claim 1, wherein
said electronic transaction data is a DICOM compatible transaction and said genomic information is associated with medical data of said first patient in said DICOM compatible transaction.

8. A system for managing patient healthcare data suitable for use in a hospital information system, comprising:
   a first database including mapping information supporting conversion of genomic information in a first data format to a different second data format;
   an interface for receiving electronic transaction data including data representing genomic information indicating identity of a first patient in a first data format, said genomic information being associated with medical data of said first patient;
   a repository including a record of a particular patient incorporating medical data and data representing genomic information indicating identity of said particular patient in a second data format different to said first data format; and
   a data processor, electronically coupled to said interface and said repository, for,
      applying said mapping information in converting said genomic information indicating identity of said first patient to said second data format,
      comparing said genomic information indicating identity of said particular patient with converted received data representing genomic information associated with medical data of said first patient,
      identifying a genomic match indicating said first patient and said particular patient are the same patient in response to the comparison and predetermined matching criteria, and
   initiating storage of said medical data of said first patient in said record of said particular patient in response to said genomic match and merging of at least a portion of said record of said particular patient with another record of said particular patient in response to said genomic match patient in response to said genomic match to provide a merged record by employing terms, codes, or identifiers that are predefined in the system and that facilitate the integration of clinical and genetic data.

9. A system according to claim 8, wherein
said electronic transaction data comprises at least one of, (a) an HL7 compatible message and (b) a DICOM compatible message and
said mapping information includes at least one of, (a) codes, (b) terms, and (c) identifiers derived from a plurality of different sources and supporting interpretation of genomic information derived from different sources and facilitating the integration of person, clinical, and genetic data.

10. A system according to claim 8, wherein said electronic transaction data is an HL7 compatible transaction and said genomic information is associated with medical data of said first patient in said HL7 compatible transaction.

11. A system according to claim 8, wherein said electronic transaction data is a DICOM compatible transaction and said genomic information is associated with medical data of said first patient in said DICOM compatible transaction.

12. A system for managing patient healthcare data suitable for use in a hospital information system, comprising:
- a first database including mapping information supporting conversion of genomic information in a first data format to a different second data format;
- an interface for receiving HL7 or DICOM compatible electronic transaction message data including data representing genomic information indicating identity of a first patient in a first data format, said genomic information being associated with medical data of said first patient by said electronic transaction message data;
- a repository including a record of a particular patient incorporating medical data and data representing genomic information indicating identity of said particular patient in a second data format different to said first data format; and
- a data processor, electronically coupled to said interface and said repository, for,
  - applying said mapping information in converting said genomic information indicating identity of said first patient to said second data format,
  - comparing said genomic information indicating identity of said particular patient with converted received data representing genomic information associated with medical data of said first patient,
  - identifying a genomic match indicating said first patient and said particular patient are the same patient in response to the comparison and predetermined matching criteria, and
- initiating storage of said medical data of said first patient in said record of said particular patient in response to said genomic match and merging of at least a portion of said record of said particular patient with another record of said particular patient in response to said genomic match patient in response to said genomic match using terms, codes, or identifiers that are predefined in the system and that facilitate the integration of clinical and genetic data, to provide a merged record.

* * * * *